(12) United States Patent
Boeke et al.

(10) Patent No.: US 11,814,644 B2
(45) Date of Patent: Nov. 14, 2023

(54) EXTRACHROMOSOMAL SWITCHING AUXOTROPHIES PROGRESSIVELY BY INTEGRATION (ESWAP-IN) FOR ASSEMBLY OF DNA SEQUENCES IN YEAST

(71) Applicant: New York University, New York, NY (US)

(72) Inventors: Jef D. Boeke, New York, NY (US); Leslie A. Mitchell, New York, NY (US); Neta Agmon, New York, NY (US)

(73) Assignee: New York University, New York, NY (US)

( * ) Notice: Subject to any disclaimer, the term of this patent is extended or adjusted under 35 U.S.C. 154(b) by 1168 days.

(21) Appl. No.: 16/315,844

(22) PCT Filed: Jul. 7, 2017

(86) PCT No.: PCT/US2017/041117
§ 371 (c)(1),
(2) Date: Jan. 7, 2019

(87) PCT Pub. No.: WO2018/009809
PCT Pub. Date: Jan. 11, 2018

(65) Prior Publication Data
US 2019/0300909 A1    Oct. 3, 2019

Related U.S. Application Data

(60) Provisional application No. 62/359,264, filed on Jul. 7, 2016.

(51) Int. Cl.
| | | |
|---|---|---|
| C12N 15/90 | (2006.01) | |
| C12N 1/16 | (2006.01) | |
| C12N 15/64 | (2006.01) | |
| C12N 15/65 | (2006.01) | |
| C12N 15/66 | (2006.01) | |
| C12N 15/81 | (2006.01) | |
| C12N 15/85 | (2006.01) | |

(52) U.S. Cl.
CPC ............ *C12N 15/905* (2013.01); *C12N 1/16* (2013.01); *C12N 15/64* (2013.01); *C12N 15/65* (2013.01); *C12N 15/66* (2013.01); *C12N 15/81* (2013.01); *C12N 15/85* (2013.01); *C12N 15/90* (2013.01)

(58) Field of Classification Search
None
See application file for complete search history.

(56) References Cited

U.S. PATENT DOCUMENTS

| | | |
|---|---|---|
| 2005/0148062 A1 | 7/2005 | Contreras et al. |
| 2016/0046972 A1 | 2/2016 | Boeke et al. |
| 2017/0226532 A1 | 8/2017 | Boeke et al. |

OTHER PUBLICATIONS

Annaluru, N., et al., Total Synthesis of a Functional Designer Eukaryotic Chromosome, Science, Apr. 4, 2014, vol. 344, No. 6179, pp. 55-58.

Mitchell. L.A., et al., Versatile genetic assembly system (VEGAS) to assemble pathways for expression in *S. cerevisiae*, Nucleic Acid Research, May 8, 2015, vol. 43, No. 13, pp. 6620-6630.

*Primary Examiner* — Nancy J Leith
(74) *Attorney, Agent, or Firm* — Hodgson Russ LLP

(57) ABSTRACT

Compositions, methods and kits are provided. The compositions, methods and kits are for assembly of series of DNA segments in yeast using homologous recombination. The assembled DNA segments are maintained episomally. Yeast made using the methods are included, as are methods of using the yeast to express proteins, and for screening test agents that can affect yeast that are modified to include the assembled DNA segments.

7 Claims, 11 Drawing Sheets
Specification includes a Sequence Listing.

Step 1a

Step 1b

```
                              SEQUENCE LISTING

<160> NUMBER OF SEQ ID NOS: 4

<210> SEQ ID NO 1
<211> LENGTH: 198
<212> TYPE: DNA
<213> ORGANISM: artificial sequence
<220> FEATURE:
<223> OTHER INFORMATION: sequence orthogonal to yeast genome

<400> SEQUENCE: 1
aaggtagcta ccaatattta gtttctaagc cttgcgacag acctcccact tagattgcca      60
cgcatagagc tagcgagtca gcgaaaagca tgacgcgctt tcaagcgtgg cgagtatgtg     120
aaccaaggct tcggacagga ctatatactt aggtttgatc tcgccccgag aactgtaaac     180
ctcaacattt atagatta                                                   198

<210> SEQ ID NO 2
<211> LENGTH: 239
<212> TYPE: DNA
<213> ORGANISM: artificial sequence
<220> FEATURE:
<223> OTHER INFORMATION: sequence orthogonal to yeast genome

<400> SEQUENCE: 2 cccttaggt tgcaaatgct ccgtcgacgg gatctgtcct tctctgccgg cgatcgtgga       60
ggtactggcc tagcgtcgtg gcccgggaga gacagtttag tagtgactcg cggctccgga    120
tccctttcgg tccatatagc ggatttccat agacgtagac cgcgccaatg tgattaaggg    180
gcataccgtg cctatcctgg taattgtgta ggctacctgt ctgtatacgc gtactggcc     239

<210> SEQ ID NO 3
<211> LENGTH: 200
<212> TYPE: DNA
<213> ORGANISM: artificial sequence
<220> FEATURE:
<223> OTHER INFORMATION: sequence orthogonal to yeast genome

<400> SEQUENCE: 3
tttagggtag catcaggaat ctgaaccctc agaaagtggg gatcccgggt atagaccttt      60
atctgcggtt caagttaggc ataaggctgc atgctacctt gtcacaccta cactgctcga    120
agtaaatatg ggaagcgtgc gacctggctc caggcgttcc gcgccgccac gtgttcgtta    180
actgttgatt ggtggcacat                                                200

<210> SEQ ID NO 4
<211> LENGTH: 285
<212> TYPE: DNA
<213> ORGANISM: artificial sequence
<220> FEATURE:
<223> OTHER INFORMATION: sequence orthogonal to yeast genome

<400> SEQUENCE: 4
tgacgcttgg atgcgtgacc ccgtacgtca tgacccgtca tgggtatgta agcgaagttg      60
gcgttaattg tagcttattt cccgccctgt gattgaggcg ggatggtgtc cccatgcacg    120
gcgctaggtg tgatatcgta cacttgggag aagtcagata cgattgcggc ttagcggcgc    180
cgggaaatcc agcatattct cgcggccctg agcagtaggt gtctcgggga gtctacgtta    240
cacctgaact cgcatgtctg gggttgtggt caggccttgt caatt                    285
```

EXTRACHROMOSOMAL SWITCHING AUXOTROPHIES PROGRESSIVELY BY INTEGRATION (ESWAP-IN) FOR ASSEMBLY OF DNA SEQUENCES IN YEAST

CROSS REFERENCE TO RELATED APPLICATIONS

This application claims priority to U.S. provisional application No. 62/359,264, filed Jul. 7, 2016, the disclosure of which is incorporated herein by reference.

STATEMENT REGARDING FEDERALLY SPONSORED RESEARCH

This invention was made with government support under Grant Number MCB-1441866 awarded by the National Science Foundation. The government has certain rights in the invention.

SEQUENCE LISTING

The instant application contains a sequence listing which has been submitted in .txt format and is hereby incorporated by reference in its entirety. Said .txt file is named "058636.00108-ESWapIN_PCT", was created on Jul. 10, 2017, and is 2,191 bytes in size.

FIELD OF THE DISCLOSURE

The disclosure generally relates to enhanced recombinant molecular biological approaches to manipulating genetic content. More particularly the disclosure generally relates to the assembly of multiple large segments of DNA by homologous recombination in yeast assembly of multiple large segments of DNA.

BACKGROUND

There is an ongoing and unmet need to provide compositions and methods for producing large segments of DNA that are useful for a wide variety of applications. The present disclosure is pertinent to this need.

SUMMARY OF THE DISCLOSURE

The present disclosure provides compositions and methods for introducing large segments of DNA into yeast by in part taking advantage of the capability of yeast to perform homologous recombination. The segments are assembled in a stepwise fashion using DNA segments that can be homologous recombined in yeast in an order and manner dictated in part by having terminal ends that have homology to one another, but not to the yeast genome in which homologous recombination of the segments occurs, and not to a vector component that is used to circularize the assembled segments and accordingly facilitate their maintenance in yeast as extrachromosomal elements. Thus, the invention utilizes consecutive rounds of homologous recombination to introduce additional DNA segments, and to iteratively replace an introduced selectable marker. This allows marker recycling over successive steps as the length of assembled DNA construct becomes progressively longer.

In certain embodiments the disclosure provides a method as shown in FIG. 2, wherein the BAC component is optional, and wherein the LEU2, URA3, and KANr markers are non-limiting illustrations of selectable markers that can be substituted with other auxotrophic or otherwise selectable markers, as will be apparent to those skilled in the art from the present disclosure. In certain embodiments the disclosure provides vectors that are depicted in FIG. 6, wherein the BAC component is optional, and wherein the particular labeled genetic elements provide non-limiting illustrations of selectable markers and other genetic elements.

In certain approaches the disclosure involves use of sequences that are orthogonal to the yeast genome, and are moreover orthogonal to the DNA segments that are recombined in the yeast. In embodiments the orthogonal sequences are characterized by not being present in the yeast genome in which recombination takes place, and also by having about 45-55% GC content over at least 40 bp segment, such as a sliding 40 bp window across the length of the segment, which can be up to 200 bp, or longer. The orthogonal sequences may also have no homopolymer segments that are longer than 5 bp, no instances of BsaI:AarI:BceAI:SalI:XhoI:BsmBI:NotI:I-SceI sites, and none of the orthogonal sequences are the same as each other, i.e., the sequences do not fully align to each other. In embodiments, a vector and/or a DNA segment(s) that is recombined into a vector in yeast as comprises at least one sequence of at least 40 consecutive nucleotides of SEQ ID NO:1, SEQ ID NO:2, SEQ ID NO:4, or SEQ ID NO:4, or 40 consecutive nucleotides of a sequence that is from 80%-99% similar to at least one of these sequences, provided the sequences remain orthogonal to the yeast genome, and to the DNA segments that are recombined.

BRIEF DESCRIPTION OF THE FIGURES

(FIG. 4A) Regulatory elements including CTCF binding sites and DNase hypersensitive elements are shown. Tiling of ~3 kb amplicons across locus indicated. (FIG. 4B) 38 x~3 kb PCR amplicons spanning the 100 kb HPRT locus generated from genomic DNA from HEK293T cells. Amplicons overlap each other by a minimum of 80 bp so as to be compatible with eSwAP-In assembly in yeast. Missing/faint amplicons were generated in a separate experiment using optimized PCR conditions. (FIG. 4C) Strategy to assemble HPRT in 3 steps of eSwAP-In. (FIG. 4D) After each assembly step (steps 1-3), the resulting DNA constructs from yeast were recovered into *E. coli*. Constructs (step 1 pLM718; step 2 pLM747; step 3 pLM750) were prepped and digested with PacI restriction enzyme. Field inversion gel electrophoresis (FIGE) was used to separate the resulting which ran exactly as predicted (step 1: 31 kb, 16 kb; step 2: 43 kb, 24 kb, 16 kb; step 3: 46 kb, 24 kb, 19 kb, 16 kb, 7 kb). (FIG. 4E) Strategy to screen yeast colonies derived from assembly experiments, focusing on those with the correct genotype (e.g. Leu+/Ura– or Ura+/Leu–). Primers (red arrows) spanning assembly junctions are used to test for presence/absence of amplicons in many independent yeast colonies. (FIG. 4F) One yeast colony from HPRT eSwAP-In step 3 (Ura+/Leu–) was tested with primers for all indicated assembly junctions. All expected amplicons are present.

(FIG. 5A) Schematic of the mouse alpha globin locus. Thirty-two ~4 kb PCR amplicons were produced from a previously existing BAC template. Four synthetic modules were designed to delete specific enhancer elements (Δenh1-4) were produced by fusion PCR. (FIG. 5B) In three steps of eSwAP-In the two loci were assembled. The 5' end of each construct encodes a loxP site (triangle), half of the selectable HPRT gene (3' HPRT) and a FLP site (half triangle left of 3'HPRT). The 3' end of each construct encodes a thymidine kinase gene (TK) and a heterotypic lox site (triangle). These flanking sequences enable deliver to a pre-existing 'landing pad' sequence in a mouse embryonic stem cell. (FIG. 5C) Predicted SwaI digestion patterns for the wild type (WT), synthetic (SYN) and parental BAC sequences. (Fig. D) Field inversion gel electrophoresis SwaI digestion patterns of two independent isolates of WT and SYN alpha globin constructs compared to the parental BAC. Marker sizes are indicated in kilobases (kb).

FIGS. 6A, 6B, and 6C depict genetic parts for maintenance in *E. coli* which include a kanamycin resistance (KanR) gene plus a bacterial artificial chromosome (BAC) sequence for low copy number maintenance. For replication and segregation in yeast the vectors encode a selectable marker (LEU2 as a non-limiting example, but any yeast selectable marker can be used) plus a centromere and autonomously replicating sequence (CEN/ARS). The vectors can be linearized by digestion with I-SceI, which will release the yeast selectable marker and expose left and right assembly arm sequences that are orthogonal in sequence to the yeast genome and to the DNA that is being assembled. (FIGS. 6B and 6C) A puromycin cassette (PURO) allows for selection in mammalian cells. (FIG. 6C) The self-replicating viral-based Epstein-Barr cassette (OriP/EBNA) enables long-term episomal persistence in human cells.

DESCRIPTION OF THE INVENTION

Unless defined otherwise herein, all technical and scientific terms used in this disclosure have the same meaning as commonly understood by one of ordinary skill in the art to which this disclosure pertains.

Every numerical range given throughout this specification includes its upper and lower values, as well as every narrower numerical range that falls within it, as if such narrower numerical ranges were all expressly written herein.

The disclosure includes all steps and compositions of matter described herein in the text and figures of this disclosure, including all such steps individually and in all combinations thereof, and includes all compositions of matter including but not necessarily limited to vectors, cloning intermediates, cells, cell cultures, etc.

The terms "rightmost" and "right" end, and "leftmost" and "left" end are for convenience of reference and pertain to the figures and embodiments of this disclosure. It will be recognized that the sequences presented herein are given in the 5'-3' direction, but because the sequences are typically double stranded during operation of the invention they have a complementary sequence that is in the 3'-5-direction, and such complementary sequences are encompassed by this disclosure.

Figure 1:
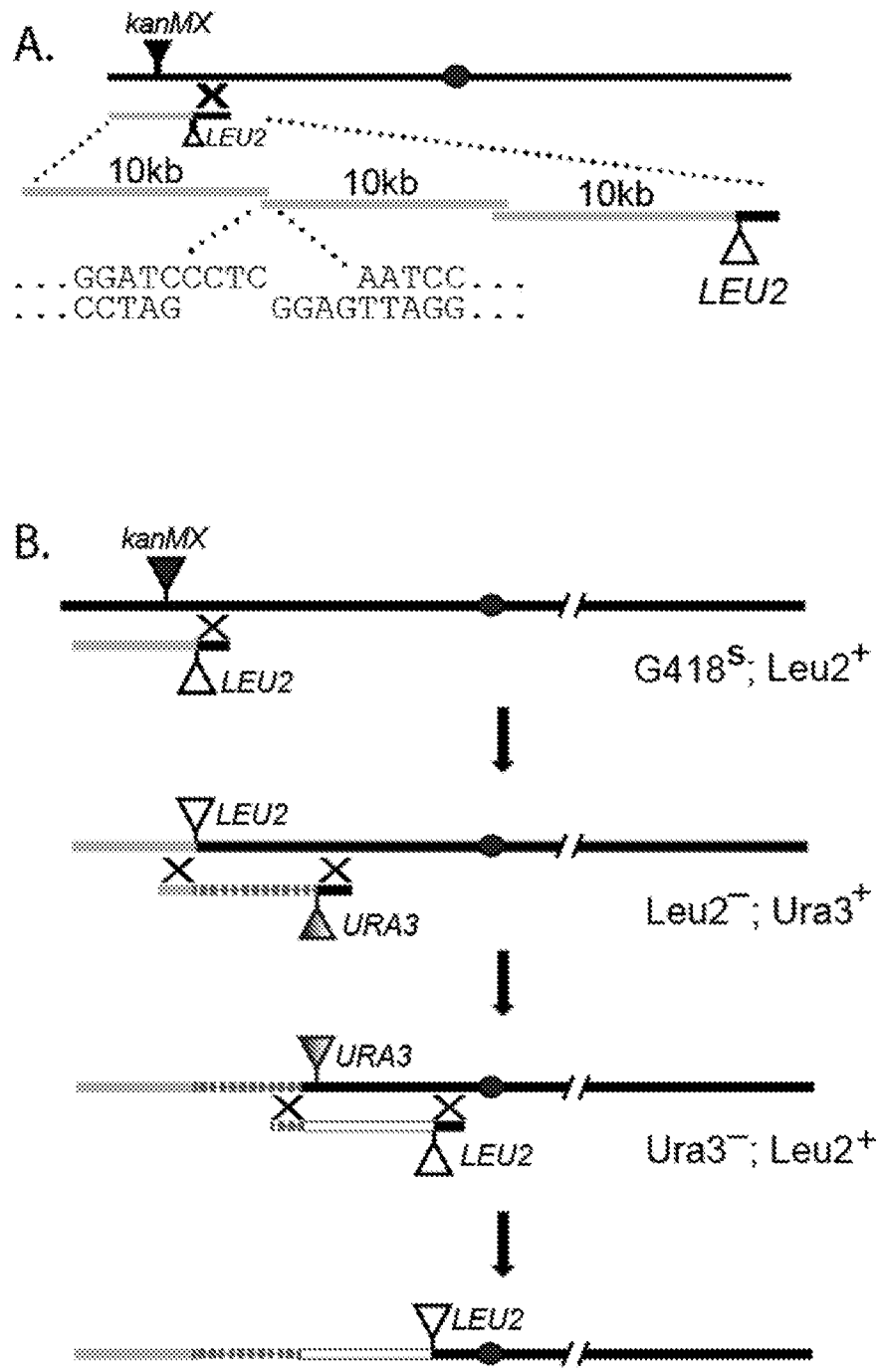
FIG. 1: SwAP-In (FIGS. 1A and 1B) compared to eSwAP-In (FIGS. 1C and 1D).
Figure 1:
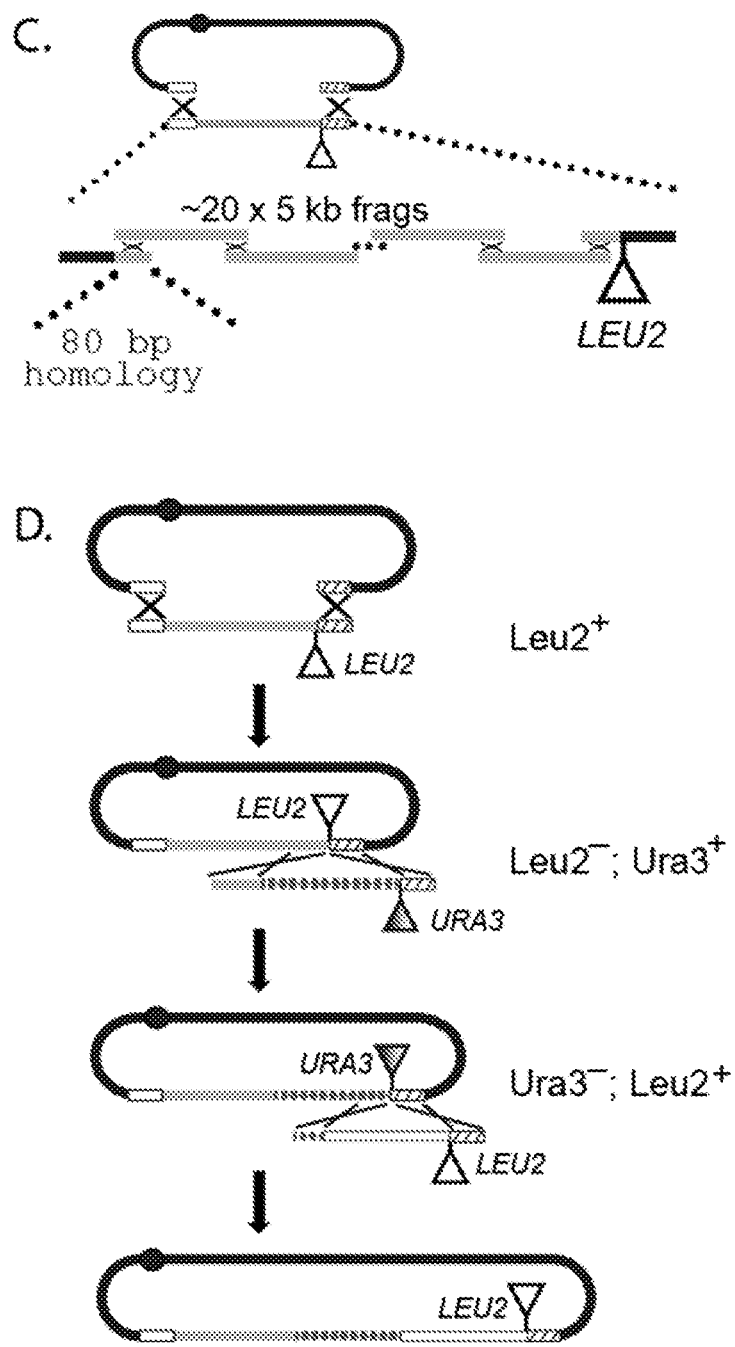
Figure 2:
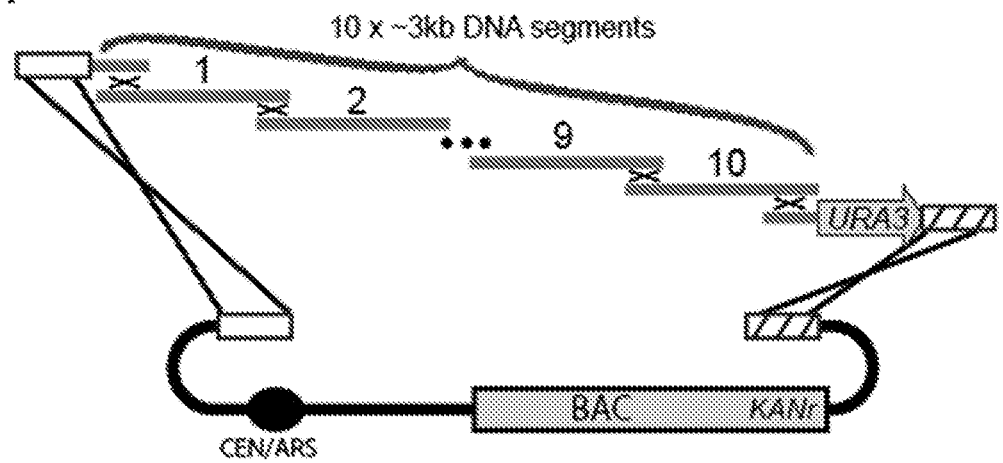
FIG. 2: eSwAP-In schematic.
Figure 2:
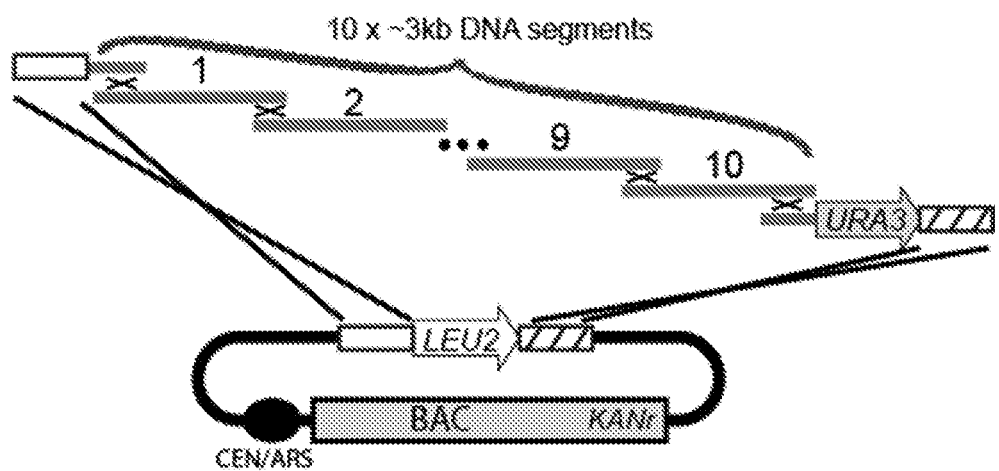
Figure 2:
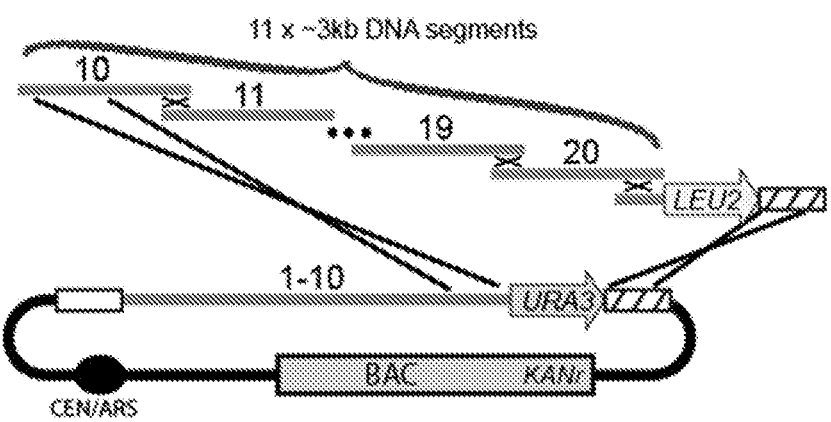
Figure 2:
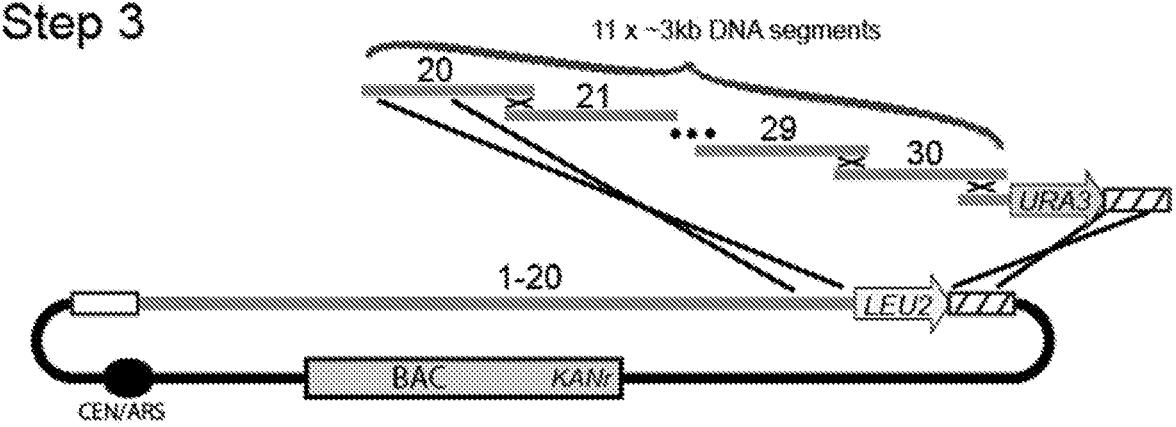

The inherent capacity of *S. cerevisiae* to perform homologous recombination (HR) can be harnessed for the process of DNA assembly. With a minimum of 40 base pairs of terminal sequence homology encoded by adjacent parts, *S. cerevisiae* can act as a cloning vehicle and stitch together arbitrary DNA sequences of interest. The present disclosure takes advantage of the HR mechanism to provide, in certain embodiments, processes for assembly of DNA in yeast referred to herein as "eSwAP-In", standing for extrachromosomal Switching Auxotrophies Progressively by Integration.

eSwAP-In comprises several features as described further herein. One is the iterative use of two different auxotrophic markers embedded near the right most ends of DNA segments that are designed for stepwise assembly. Each successive round of assembly in yeast overwrites the previously introduced selectable marker, enabling marker recycling as the length of assembled DNA construct becomes progressively longer. A second feature of eSwAP-In is that the DNA of interest is assembled extrachromosomally and thus replicates and segregates independently of the sixteen native yeast chromosomes.

eSwAP-In improves upon a previously available approach termed SwAP-In (Dymond et al., 2011; Mitchell et al., 2017; Richardson et al., 2017). A comparison of the SwAP-In approach is generally illustrated in FIG. 1, panel A and B, while eSwAP-In is generally illustrated in FIG. 1, panel C and D and more specifically in FIG. 2. In particular, FIG. 1 panel A and panel B illustrate SwAP-In to assemble synthetic yeast chromosomes by replacing native chromosomes in a step-wise process with segments of synthetic DNA. Large segments of DNA, referred to herein as "megachunks" composed of 3-4 smaller DNA segments (i.e., "chunks") each with terminal, non-palindromic, unique restriction sites, are first assembled by in vitro ligation and then transformed into yeast to replace the corresponding native segment (black line in FIG. 1, panel A and B) by homologous recombination (represented by the large X in FIG. 2 panel A and panel B). The right-most chunk of each megachunk encodes as selectable marker for primary selection and the leftmost chunk overwrites a pre-existing marker (e.g. KanMX in (FIG. 1 panel B)). Chromosomes may be assembled from left to right in sequential steps, alternating between URA3 and LEU2. FIG. 1, panels C and D demonstrate the eSwAP-In extrachromosomal aspect of the disclosure, features of which are further illustrated by reference to FIG. 1. Thus, in contrast to SwAP-In, which modifies native yeast chromosomes, eSwAP-In is used to assemble extrachromosomal constructs that replicate and segregate alongside the native yeast chromosomes. In this regard, FIG. 2 provides a non-limiting illustration of an embodiment of the eSwAP-In approach of this disclosure via three Steps. Step 1 shows a linearized eSwAP-In assembly vector (further details of which are provided in FIG. 6) encoding parts for replication and segregation in yeast (centromere, CEN; autonomously replicating sequence, ARS) and *E. coli* (kanamycin resistance, KANr; an optional bacterial artificial chromosome (BAC) sequence) which is co-transformed with multiple overlapping segments of DNA for assembly. The leftmost segment encodes terminal sequence homology to an arm of the assembly vector (white box) and the rightmost segment encodes a yeast selectable marker (URA3) plus terminal sequence homology to the other end of the linear assembly vector (hatched box). The terminal sequence homology sequences are orthogonal to the yeast genome, meaning the sequences of the terminal sequences do not occur in the yeast in which the homologous recombination occurs. The terminal homology sequences are also orthogonal to the DNA segments that are assembled using the method of this disclosure, thus the sequence of the terminal homology sequences do not appear in the yeast genome or the DNA segments that are recombined as outlined in FIG. 2. Step 1b is an alternative to Step 1a and allows for the assembly vector to be already present at the start of the process. Thus, assembly vectors of this disclosure can be used in intact or linearized form, either of which may be introduced into yeast. In either case, assembly occurs by homologous recombination in yeast with selection on SC-Ura plates, although any other auxotrophic marker could be used instead of Ura. In Step 2 the next set of DNA segments for assembly are co-transformed into yeast carrying the assembled construct from Step 1. The left most segment of the incoming DNA in step 2 matches sequence pre-existing from the previous assembly and the right most segment encodes a second selectable marker (LEU2 in this example) plus terminal sequence homology to the eSwAP-IN assembly vector (hatched box). Assembly occurs by homologous recombination in yeast with selection on SC-Leu plates. In Step 3, which is similar to Step 2, the next set of DNA segments are co-transformed into yeast but the marker on the left most fragment is switched to URA3. This process can be repeated, switching between URA3 and LEU2 selection markers (or any other distinct marker pairs) until the desired DNA construct is assembled in its entirety. By assembling DNA sequence extrachromosomally, and in particular in a circular format using eSwAP-In, the assembled molecule can be recovered into *E. coli* or any other bacteria that are known in the art to be suitable for DNA vector propagation.

The disclosure is not particularly limited to any type of yeast. In embodiments, the yeast are any species, type or strain of *Saccharomyces*, including but not limited to *Saccharomyces cerevisiae*. Other yeast or fungi include but are not limited to species in the following genera: *Pichia, Candida, Saccharomycopsis, Schizosaccharomyces, Hansenula, Torula, Ashbya, Neurospora, Aspergillus, Penicillium*, and *Cryptococcus*.

The disclosure is not particularly limited to any size of DNA that can be made into an extrachromosomal element using the compositions and methods of this disclosure, as depicted in FIG. 2, nor is it limited to any particular number of DNA segments that can be recombined using one or more steps of the process. In certain embodiments, from 1-100 DNA double stranded segments are combined into a vector, wherein such segments can comprise, for example, a first set of linear double stranded DNA segments comprising a first DNA segment, interior DNA segments, and a first terminal DNA segment. In embodiments, from 2-20 double stranded DNA fragments are used. In embodiments, 10-20 double stranded DNA fragments are used. In embodiments, the DNA segments that are recombined comprise from 1 kb to 100 kb, inclusive, and including all numbers of nucleotides there between. In embodiments, the DNA segments that are recombined having an approximate size of about 3 kb-10 kb. Further, other than a requirement for genetic elements described herein to make and propagate the recombined vectors as extrachromosomal elements, the sequence of the DNA to the approach is not limiting. In embodiments, the DNA segments comprise RNA polymerase templates, including but not necessarily limited RNA Polymerase II templates. In embodiments, the DNA segments encode mRNA (i.e., protein coding sequences) and can encode any fragment of a protein, a full-length protein, or a combination of proteins and/or peptides, whether or not the combination is intended to function in a combination, or individually. In embodiments, the DNA segments comprise promoters or other genetic regulatory elements, including but not necessarily limited to enhancer elements, and/or elements that have one or more functions that are inducible by applying a stimulus, including but not necessarily limited to a chemical agent such as a drug or other test compound, or a change in nutrients, or an enzymatic substrate, etc., or a detectable marker, such as a protein that produced a visually detectable signal, including but not limited to a fluorescent signal. Thus, in embodiments, yeast modified according to the methods of this disclosure can produce useful proteins, and the proteins can moreover participate in the production of non-protein compounds, such as by enzymatic activity.

In certain embodiments, the DNA segments that in vectors of this disclosure comprise left end and right end sequences that are orthogonal to yeast genome, wherein recombination of the linearized vector and assembled DNA segments takes place as generally shown in FIG. 2. In embodiments, the orthogonal sequence is from 40-200 nucleotides in length, inclusive, and including all integers and ranges of integers there between, but longer lengths can be used. Thus, in certain embodiments, a vector and/or a DNA segment described herein can comprise or consist of 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 or more nucleotides in length.

In certain embodiments, DNA segments of this disclosure (i.e., the assembly arms) that are orthogonal to the yeast genome (and to the DNA segments that are recombined) are determined according to the following parameters:

(i) the sequences do not exist in the yeast genome in which recombination takes place;

(ii) the sequences have ~45-55% GC content, which can be determined in for example, a 40 bp sliding windows across the length of, for example, a 200 bp sequence or other length of sequence described herein;

(iii) no homopolymer segments that are longer than 5 bp (iv) no instances of BsaI:AarI:BceAI:SalI:XhoI:BsmBI:NotI:I-SceI sites (v) the sequences for use in the method do not fully align to each other.

In non-limiting embodiments, the vector and/or a DNA segment that is recombined into a vector in yeast as described herein comprise, for example in assembly arms, at least one sequence that comprises or consists of at least 40 consecutive nucleotides of SEQ ID NO:1, SEQ ID NO:2, SEQ ID NO:4, or SEQ ID NO:4, or a sequence that is from 80%-99% similar to these sequences, provided the sequences remain orthogonal to the yeast genome, and to the DNA segments that are recombined. In an embodiments, the sequences are at least 90, 91, 92, 93, 94, or 95% identical to the SEQ ID Nos of this disclosure. In embodiments, the left assembly arm sequence (e.g., the white box depicted in FIG. 2, on the DNA segments and/or the assembly vector, comprises at least 40 consecutive nucleotides of either:

(SEQ ID NO: 1)
TAAGGTAGCTACCAATATTTAGTTTCTAAGCCTTGCGACAGACCTCCCAC

TTAGATTGCCACGCATAGAGCTAGCGAGTCAGCGAAAAGCATGACGCGCT

TTCAAGCGTGGCGAGTATGTGAACCAAGGCTTCGGACAGGACTATATACT

TAGGTTTGATCTCGCCCCGAGAACTGTAAACCTCAACATTTATAGATTAT
or:

(SEQ ID NO: 2)
CCCCTTAGGTTGCAAATGCTCCGTCGACGGGATCTGTCCTTCTCTGCCGG

CGATCGTGGAGGTACTGGCCTAGCGTCGTGGCCCGGGAGAGACAGTTTAG

TAGTGACTCGCGGCTCCGGATCCCTTTCGGTCCATATAGCGGATTTCCAT

AGACGTAGACCGCGCCAATGTGATTAAGGGGCATACCGTGCCTATCCTGG

TAATTGTGTAGGCTACCTGTCTGTATACGCGTACTGGCC

In embodiments, the right assembly arm sequence (e.g., the hatched box depicted in FIG. 2, on the DNA segments and/or the assembly vector, comprises at least 40 consecutive nucleotides of either:

(SEQ ID NO: 3)
TTTAGGGTAGCATCAGGAATCTGAACCCTCAGAAAGTGGGGATCCCGGGT

ATAGACCTTTATCTGCGGTTCAAGTTAGGCATAAGGCTGCATGCTACCTT

GTCACACCTACACTGCTCGAAGTAAATATGGGAAGCGTGCGACCTGGCTC

CAGGCGTTCCGCGCCGCCACGTGTTCGTTAACTGTTGATTGGTGGCACAT
or:

(SEQ ID NO: 4)
TGACGCTTGGATGCGTGACCCCGTACGTCATGACCCGTCATGGGTATGTA

AGCGAAGTTGGCGTTAATTGTAGCTTATTTCCCGCCCTGTGATTGAGGCG

GGATGGTGTCCCCATGCACGGCGCTAGGTGTGATATCGTACACTTGGGAG

AAGTCAGATACGATTGCGGCTTAGCGGCGCCGGGAAATCCAGCATATTCT

CGCGGCCCTGAGCAGTAGGTGTCTCGGGGAGTCTACGTTACACCTGAACT

CGCATGTCTGGGGTTGTGGTCAGGCCTTGTCAATT

It will be apparent from the foregoing that these orthogonal sequences can be present on a vector (whether circular or linearized) and serve as first and second recombination sequences that are non-homologous to the yeast genome. These orthogonal sequences can also be present in a first set of linear double stranded DNA segments comprising a first DNA segment, interior DNA segments, and a first terminal DNA segment, wherein the first DNA segment comprises at its left end a sequence homologous to the first recombination sequence in the vector (i.e., the white box of FIG. 2) and at its right end a sequence that is homologous to a left end of a first interior DNA segment (i.e., the hatched box of FIG. 2) such that recombination between linearly recombined DNA segments shown in FIG. 2 are recombined appropriately with the homologous sequences in the vector, also depicted in FIG. 2, as well as in FIG. 6.

In embodiments the disclosure comprises assembling DNA segments using the eSwAP-In approach as described herein to obtain yeast that comprise the recombined extrachromosomal elements produced using the method depicted in FIG. 2. In embodiments, the disclosure further comprises yeast comprising the recombined extrachromosomal elements.

In embodiments, the disclosure comprises liquid cell cultures and/or culture plates comprising such modified yeasts. In embodiments, the yeast are cryopreserved, or are subjected to increased temperatures to, for example, analyze temperature sensitive genetic elements. In embodiments the disclosure comprises cell culture media in which yeasts modified by the eSwAP-In approach are grown. The disclosure includes separating one or more compounds or other substances synthesized by the yeast from the cell culture media, and/or from yeast lysates, and optionally purifying any such compound to any desired degree of purity.

In one embodiment the disclosure comprises subjecting yeast made using the eSwAP-In approach as described herein to a stimulus, and determining whether or not the stimulus produces an effect in the yeast that is attributable to the extrachromosomal element. In embodiments, this screening approach is amenable to high-throughput screening, such as by providing a plurality of yeasts in separate reaction chambers, wherein each chamber comprises yeast with distinct extrachromosomal elements assembled by eSwAP-In, and adding one or more distinct test agents to the separate chambers to determine if, for example, a test agent has a particular effect. The disclosure thus comprises determining which of a plurality of DNA segments assembled using eSwAP-In may contribute to or be responsible for a response elicited by a test compound.

Figure 4:
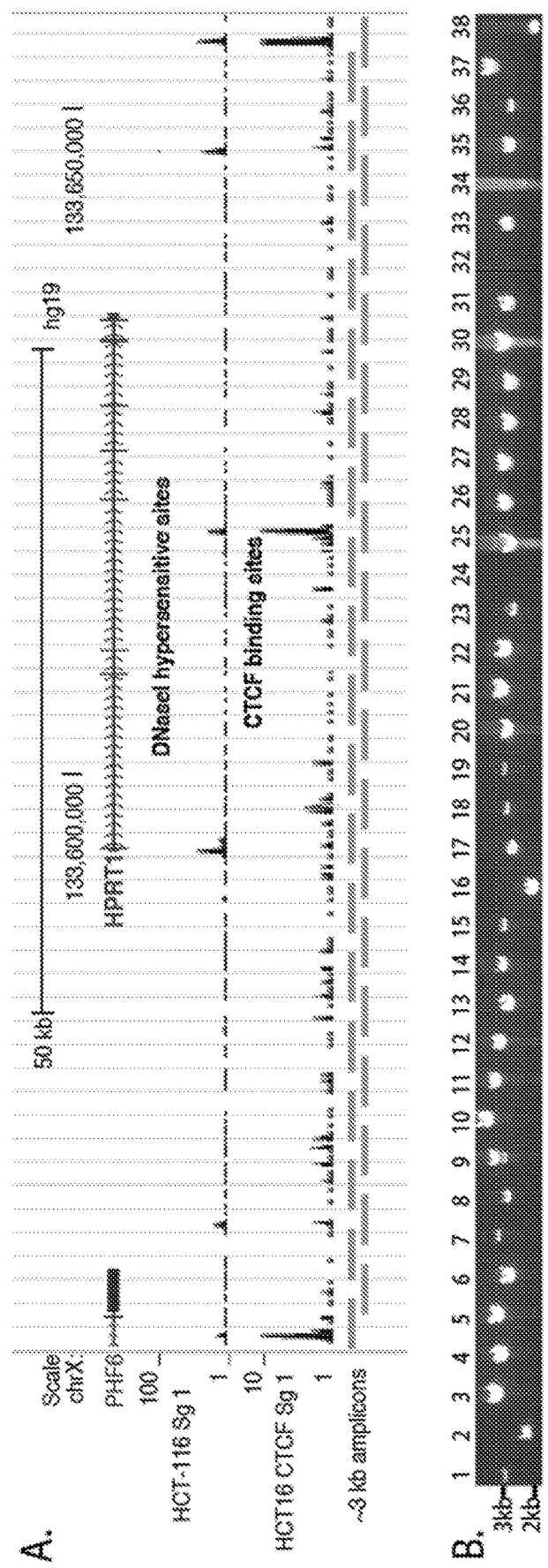
FIG. 4: Schematic depicting eSwAP-In to assembly the ~100 kb human HPRT gene locus in yeast.
Figure 4:
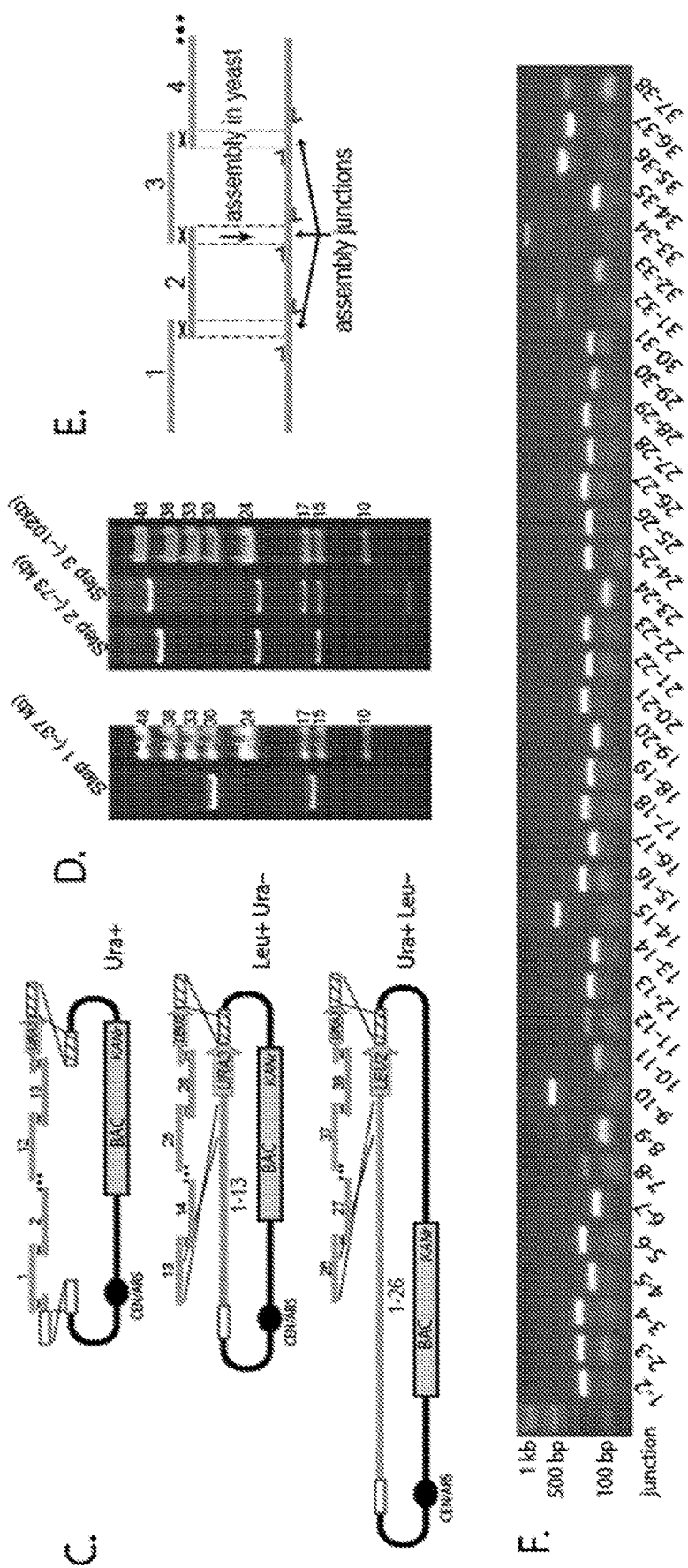
Figure 5:
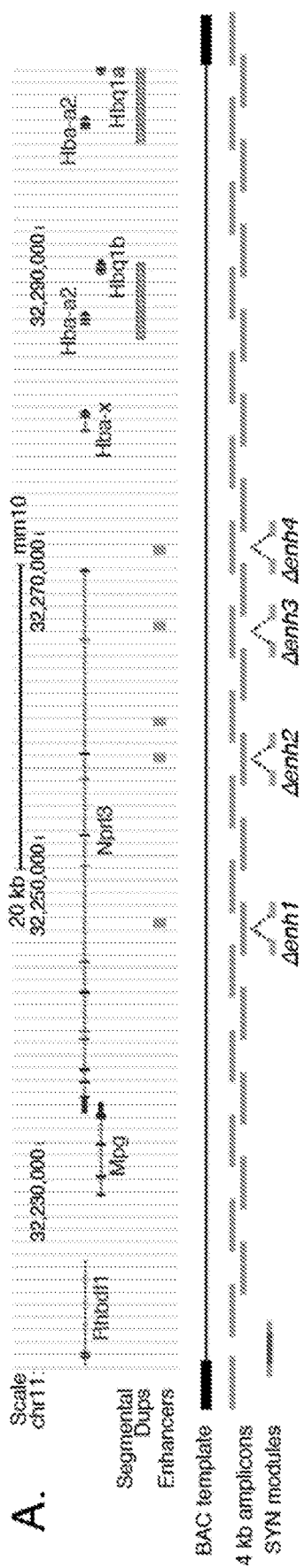
FIG. 5. eSwAP-In to assembly wild-type and synthetic versions of the mouse alpha globin locus.
Figure 5:
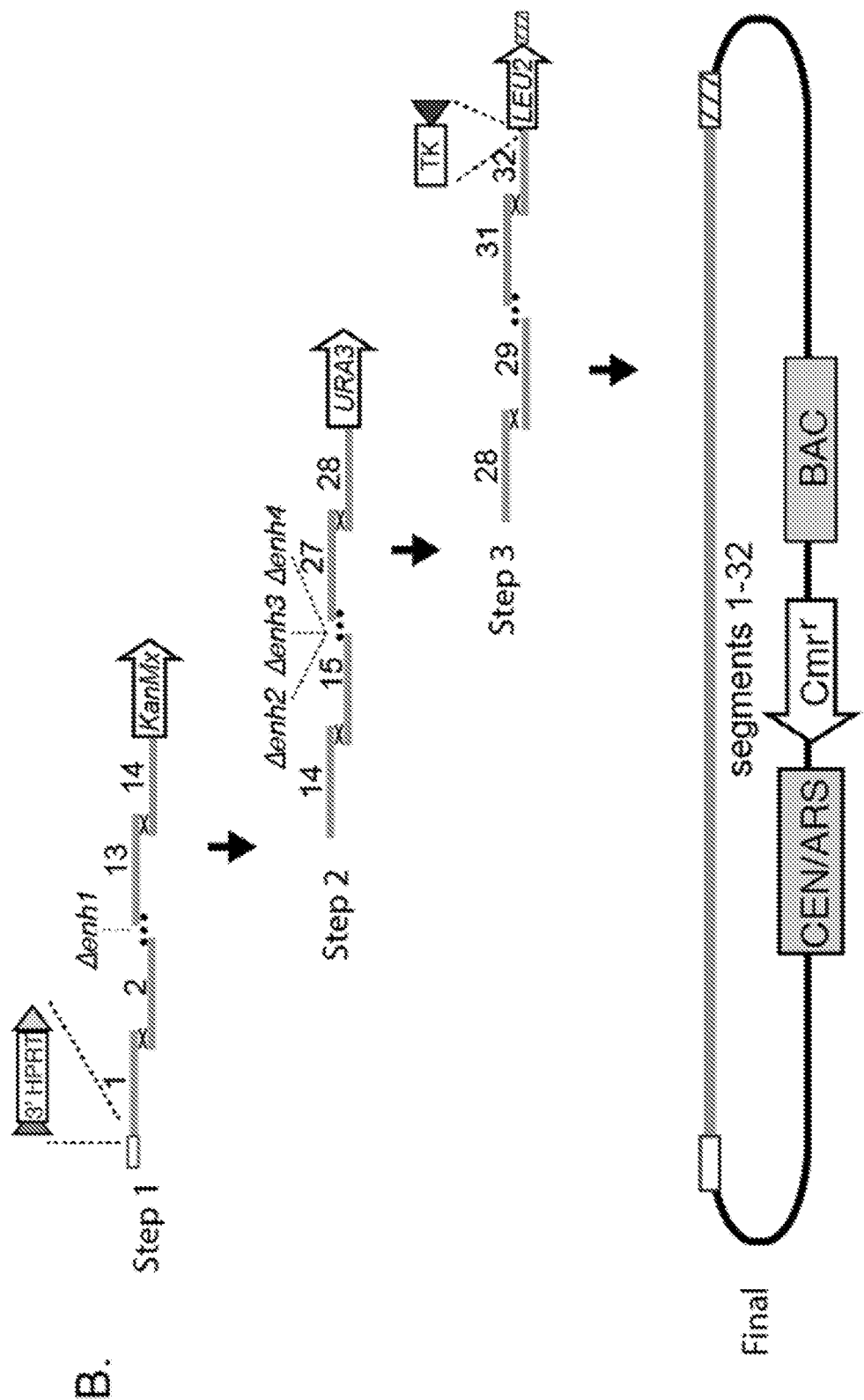
Figure 5:
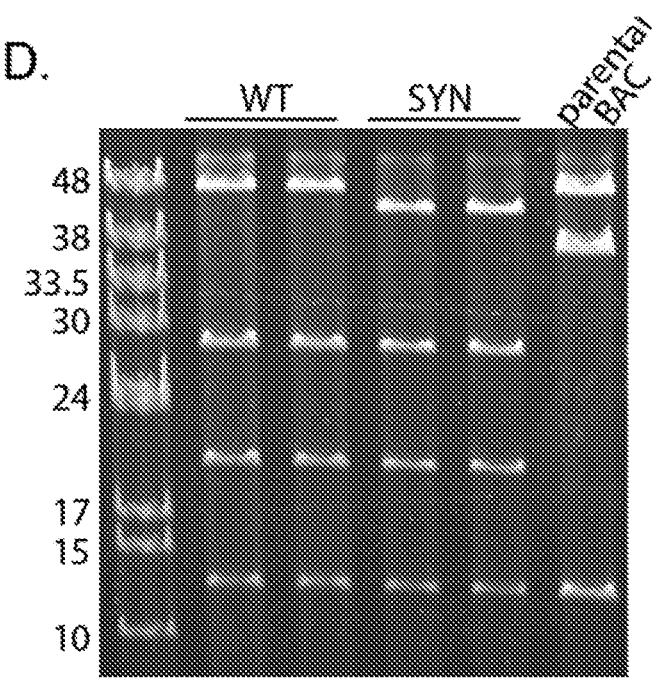

In the Examples of the present disclosure we demonstrate eSwAP-In in non-limiting illustrations applied to a two-step assembly of a metabolic pathway for expression in yeast (FIG. 3) as well as a three step assembly of a ~100 kb human genomic sequence (FIG. 4) and assembly of wild-type and synthetic versions of the mouse alpha globin locus (FIG. 5). eSwAP-In as described above includes an assembly vector(s) encoding unique sequences to serve as landing pads for assembly plus genetic features that support replication and segregation in both yeast and *E. coli*. Thus, in embodiments, DNA segments of this disclosure comprise landing pads that are used as assembly arms having the sequences described above.

The following Examples are intended to illustrate but not limit the disclosure.

Example 1

Figure 3:
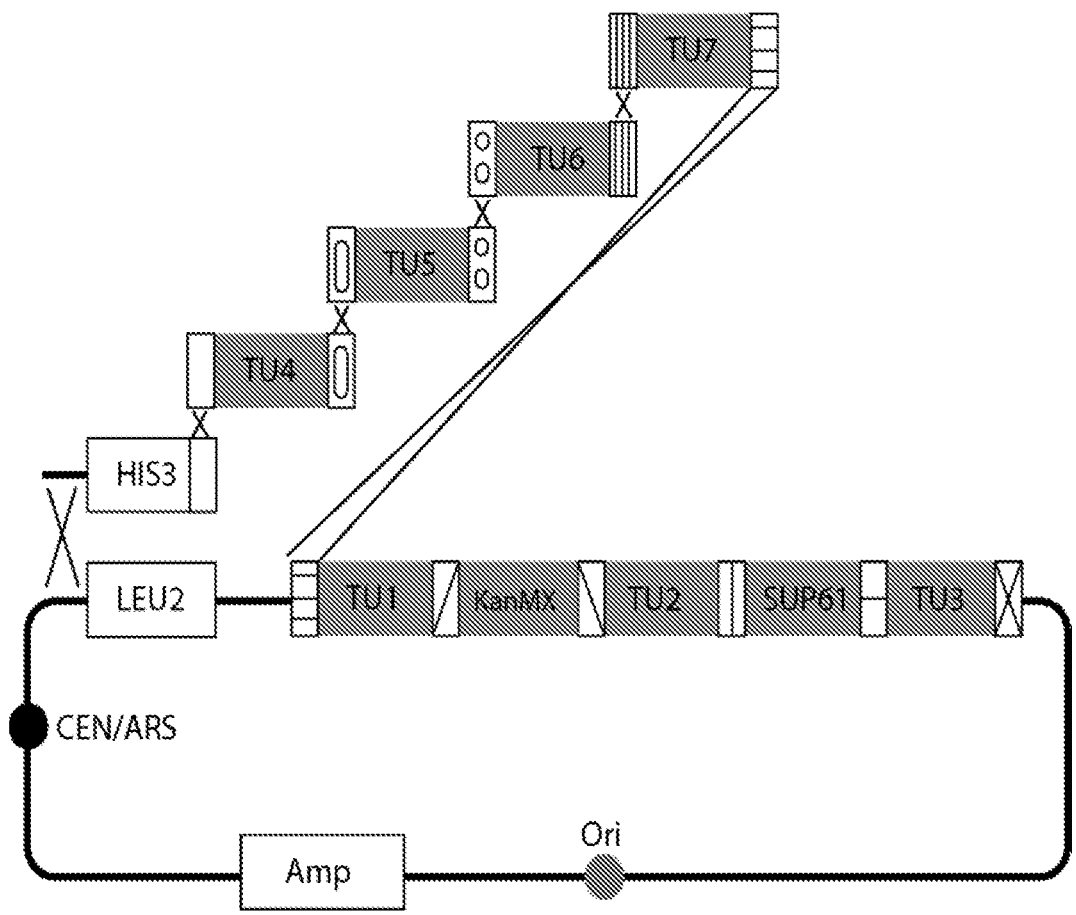
FIG. 3: Schematic depicting eSwAP-In to assemble the human de novo purine biosynthetic pathway for expression in yeast. The schematic shows a preassembled construct encoding three transcription units (TU1-TU3) of the de novo purine biosynthetic pathway, a gene to render the pathway essential (SUP61) and one marker cassette (KanMX) in a yeast shuttle vector (marked with LEU2) is expanded by eSwAP-IN using multiple preassembled transcription units (HISS, TU4-TU7). TUs for eSwAP-IN are flanked by 70 bp terminal homology between adjacent parts to enable homologous recombination in yeast (white rectangles with various hatch marks). The left most TU (HIS3) encodes homology to the left of LEU2 on the vector and the right most TU (TU7) is homologous to the right of LEU2. Co-transformation of TUs and vector into yeast followed by selection on medium lacking histidine enable assembly of the 7-gene pathway. Yeast cells are now unable to grow on medium lacking leucine and able to grow on medium lacking histidine as well as media supplemented with G418 (resistance encoded by KanMX).

This Example demonstrates cloning and assembly of human de novo purine biosynthetic pathway in yeast. This pathway includes 7 transcription units (TUs), each comprised of a human coding sequence (CDS), codon optimized for yeast expression and flanked by the orthologous yeast regulatory sequences. We first assembled 3 TUs, a gene to render the pathway essential (SUP61) and one marker cassette (KanMX) in a yeast shuttle vector marked with LEU2 by coupling two technologies we developed—yeast Golden Gate (yGG) (Agmon et al., 2015) and Versatile Genetic Assembly System (VEGAS) (Mitchell et al., 2015). Next we individually constructed the remaining four TUs and a marker cassettes (HIS3), each encoding ~70 bp of terminal sequence homology between adjacent parts to direct assembly in yeasto (FIG. 3). The sequences to the left of HIS3 marker cassette and to the right of KanMX cassette were designed to integrate on either side of the pre-existing LEU2 marker on the shuttle vector carrying the first five pathway TUs. Thus, by co-transforming these five parts into a strain already carrying the five TU construct marked with LEU2, the full nine-gene pathway was assembled (FIG. 3). This was achieved by selection on medium lacking histidine and subsequently replica plating on medium lacking leucine to identify His+ colonies no longer capable of growing in the absence of leucine. While this particular and non-limiting example required only one round of eSwAP-In, additional steps could be performed to build pathways encoding any number of genes, as depicted in FIG. 2.

Example 2

This Example demonstrates cloning and assembly of the ~100 kb HPRT1 human gene locus. HPRT1 is a conserved gene with a role in purine biosynthesis. It is well-studied since it can conveniently be selected for (in HAT medium) or against in (6-thioguanine medium), making the presence/absence of functional protein product. Mutation(s) in the HPRT1 gene, which is encoded on the human X-chromosome, lead to Lesch Nyhan disorder and gout in humans. With an aim of delivering the ~100 kb HPRT1 gene to mammalian cells to study regulatory elements associated with the human HPRT1 locus (FIG. 4A), we devised a strategy to assembly it in yeast using eSwAP-In. We generated 38 x ~3 kb amplicons spanning the HPRT1 locus (FIG. 4A) from human genomic DNA. In three sequential steps, each encompassing 12-13 individual fragments and switching between the Ura+/Leu− and Leu+/Ura− phenotypes (FIG. 4B), we assembled HPRT1 extrachromosomally in yeast (FIG. 4C-F). The constructs resulting from all three assembly steps were recovered into E. coli in order to validate their structure by digestion (FIG. 4D). For all three steps, we first screened yeast transformants for the correct auxotrophic marker phenotype (e.g. Ura+/Leu−) and subsequently tested for the presence/absence of correctly assembled constructs based on primers spanning assembly junctions (FIG. 4E). The presence of all assembly junction amplicons suggests a correctly assembled clone. We identified an independent yeast colony that encodes the entire ~100 kb HPRT1 locus based on assembly junction PCR analysis (FIG. 4F).

Example 3

This Example demonstrates cloning and assembly of wild-type and synthetic versions of the mouse alpha globin locus.

In particular, we used e-SwAP-In to assemble two versions of the ~90 kb mouse alpha globin locus in yeast, specifically a wild-type and synthetic mouse alpha globin locus (FIG. 5A). In three steps of eSwAP-In, the two x ~90 kb constructs were assembled in parallel from a total of 32 PCR amplicons or synthetic DNA fragments derived from a pre-existing BAC construct or fusion PCR (FIG. 5B). The two constructs are designed for delivery to a previously described locus in a mouse ES cell engineered for 'recombination-mediated genomic exchange' to be compatible with site-specific recombination sequences and selectable/counter-selectable markers in the mouse alpha globin loci built here (Wallace et al., 2007). The synthetic locus is distinct from the wild-type locus as it encodes the deletion of four enhancer elements. The two constructs were assembled in yeast using 3 steps of eSwAP-In (FIG. 5B) and then recovered into E. coli and digestion verified (FIG. 5C).

Example 4

Figure 6:
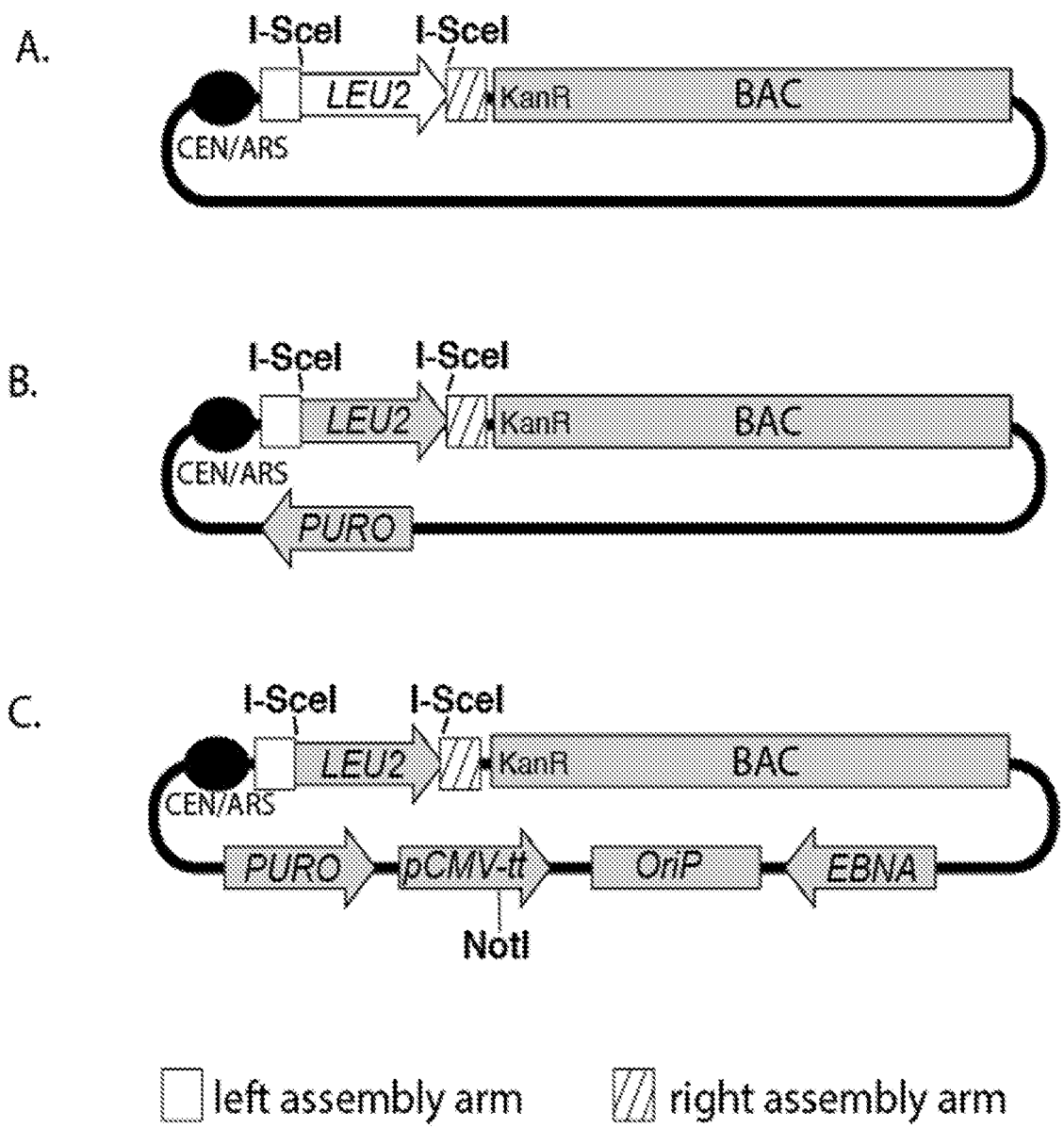
FIG. 6. eSwAP-IN assembly vectors.

This Example provides a description of vectors of this disclosure. Specifically, we designed and constructed three eSwAP-In assembly vectors that encode genetic parts for maintenance in both yeast and E. coli (FIG. 6). The three vectors are distinguished by additional parts including a mammalian selection marker (puromycin) and the self-replicating viral-based Epstein-Barr cassette (OriP/EBNA), which allows for long-term episomal persistance in human cells (FIGS. 6B and 6C). All three assembly vectors are further customized specifically for 'in yeasto' assembly and encode ~200 bp terminal landing pad sequences, also known as assembly arms, orthogonal in sequence to the yeast genome, and separated from each other another by a yeast selectable marker flanked by I-SceI sites. Digestion with I-SceI linearizes the eSwAP-In assembly vectors, exposing the terminal landing pads for in yeasto assembly of arbitrary sequence where the right-most fragment encodes a different selectable marker and the termini of the DNA fragments being assembled encode homology to the landing pads. The landing pad sequences in FIG. 6 (assembly arms) are the same as described above in connection with FIG. 2, and thus can comprise any 40-200 or longer DNA sequence that is orthogonal to the yeast genome where homologous recombination of the DNA segments and the vector takes place. In embodiments, the vector sequences comprise or consist of a sequence that is orthogonal to at least one yeast genome, and/or is selected based on the parameters described above, or is at least 40 consecutive nucleotides of SEQ ID NO:1, SEQ ID NO:2, SEQ ID NO:3, or SEQ ID NO:4, or sequences having from 80%-99% similarity thereto, provided the sequences remain orthogonal to the yeast genome.

REFERENCES

Agmon, N., Mitchell, L. A., Cai, Y., Ikushima, S., Chuang, J., Zheng, A., Choi, W. J., Martin, J. A., Caravelli, K., Stracquadanio, G., et al. (2015). Yeast Golden Gate (yGG) for the Efficient Assembly of S. cerevisiae Transcription Units. ACS synthetic biology 4, 853-859.

Dymond, J. S., Richardson, S. M., Coombes, C. E., Babatz, T., Muller, H., Annaluru, N., Blake, W. J., Schwerzmann, J. W., Dai, J., Lindstrom, D. L., et al. (2011). Synthetic chromosome arms function in yeast and generate phenotypic diversity by design. Nature 477, 471-476.

Mitchell, L. A., Chuang, J., Agmon, N., Khunsriraksakul, C., Phillips, N. A., Cai, Y., Truong, D. M., Veerakumar, A., Wang, Y., Mayorga, M., et al. (2015). Versatile genetic assembly system (VEGAS) to assemble pathways for expression in S. cerevisiae. Nucleic acids research 43, 6620-6630.

Mitchell, L. A., Wang, A., Stracquadanio, G., Kuang, Z., Wang, X., Yang, K., Richardson, S., Martin, J. A., Zhao, Y., Walker, R., et al. (2017). Synthesis, debugging, and effects of synthetic chromosome consolidation: synVI and beyond. Science 355.

Richardson, S. M., Mitchell, L. A., Stracquadanio, G., Yang, K., Dymond, J. S., DiCarlo, J. E., Lee, D., Huang, C. L., Chandrasegaran, S., Cai, Y., et al. (2017). Design of a synthetic yeast genome. Science 355, 1040-1044.

Wallace, H. A., Marques-Kranc, F., Richardson, M., Luna-Crespo, F., Sharpe, J. A., Hughes, J., Wood, W. G., Higgs, D. R., and Smith, A. J. (2007). Manipulating the mouse genome to engineer precise functional syntenic replacements with human sequence. Cell 128, 197-209.

While the invention has been described through specific embodiments, routine modifications will be apparent to those skilled in the art and such modifications are intended to be within the scope of the present invention.

What is claimed is:

1. A method for producing an extrachromosomal element that is capable of assembly in yeast comprising:
   a) providing a vector comprising a bacterial selectable marker, optionally a bacterial artificial chromosome sequence (BAC), and a first yeast selectable marker that is flanked by two restriction endonuclease digestion sites, and a centromere and an autonomously replicating sequence (CEN/ARS) that is functional in yeast, the vector comprising first and second recombination sequences that are non-homologous to the yeast's genome and wherein the first and second recombination sequences flank a second yeast selectable marker that is different from the first yeast selectable marker and the two restriction endonuclease sites when the vector is circular, the vector optionally further comprising a selectable marker that is functional in mammalian cells, and optionally further comprising a self-replicating element for maintaining episomal persistence in human cells;
   b) introducing into yeast a linearized vector of a) wherein the vector is linearized with a restriction endonuclease that excises the first yeast selectable marker:
      a first set of linear double stranded DNA segments comprising a first DNA segment, a set of interior DNA segments, and a first terminal DNA segment, the first DNA segment comprising at its left end a sequence homologous to the first recombination sequence in the vector and at its right end a sequence that is homologous to a left end of a first interior DNA segment, the set of interior DNA segments having successive left end and right end homology to one another, and the terminal DNA segment having at its right end a sequence that comprises the second yeast selectable marker and a sequence that is homologous to the second recombination sequence in the vector, and
   c) allowing homologous recombination of the linearized vector with the first DNA segment, the interior DNA segments and the terminal DNA segment such that the vector is circularized in the yeast by the homologous recombination to produce a first recombined vector comprising a replacement of the first selectable marker with the second selectable marker that is selectable in the yeast using the second yeast selectable marker incorporated into the vector via the terminal DNA segment and further screening for the loss of the first selectable marker;
   d) optionally introducing into the yeast comprising the circularized vector of c) a second set of linear double stranded DNA segments comprising interior DNA segments having successive left end and right end homology to one another, and a second terminal DNA segment having at its right end a sequence that comprises the first or a third yeast selectable marker such that the second set of linear double stranded DNA segments and the second terminal DNA segment are homologously recombined into the vector of c) to produce a second recombined vector that is selectable in the yeast by the first or third yeast selectable marker, and subsequently screening for the loss of the first or third selectable marker, and
   e) optionally repeating step d) with distinct linear double stranded DNA segments that are selectable by a yeast selectable marker not present in the vector of d).

2. The method of claim 1, further comprising performing step d).

3. The method of claim 2, further comprising performing step e).

4. The method of claim 3, wherein at least the first or the second recombination sequence that is non-homologous to the yeast genome comprises at least 40 contiguous nucleotides of SEQ ID NO:1, SEQ ID NO:2, SEQ ID NO:3, or SEQ ID NO:4.

5. The method of claim 2, wherein at least the first or the second recombination sequence that is non-homologous to the yeast genome comprises at least 40 contiguous nucleotides of a sequence that is at least 80% identical to SEQ ID NO:1, SEQ ID NO:2, SEQ ID NO:3, or SEQ ID NO:4.

6. The method of claim 1, wherein the first and second recombination sequences that are non-homologous to the yeast genome comprise at least 40 nucleotides, and wherein the first and second recombination sequences that are non-homologous to the yeast genome are characterized by:
   (i) not being present in the yeast genome wherein the homologous recombination occurs;
   (ii) have approximately 45-55% GC content in the at least 40 nucleotides;
   (iii) contain no homopolymer segments greater than 5 nucleotides in length;
   (iv) do not comprise BsaI, AarI, BceAI, SalI, XhoI, BsmBI, NotI, or I-SceI restriction enzyme recognition sites;
   (v) each having distinct sequences from one another.

7. The method of claim 1, wherein at least the first or the second recombination sequence that is non-homologous to the yeast genome comprises at least 40 contiguous nucleotides of a sequence that is at least 80% identical to SEQ ID NO:1, SEQ ID NO:2, SEQ ID NO:3, or SEQ ID NO:4.

* * * * *